(12) United States Patent
Ukai et al.

(10) Patent No.: US 8,816,674 B2
(45) Date of Patent: *Aug. 26, 2014

(54) METHOD FOR DETECTING CONCENTRATION OF PARTICLES AND DEVICE THEREFOR

(75) Inventors: Hidemi Ukai, Tokyo (JP); Takashi Fujii, Aioi (JP)

(73) Assignees: IHI Corporation, Tokyo (JP); Diesel United, Ltd., Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 13/514,095

(22) PCT Filed: Jun. 15, 2010

(86) PCT No.: PCT/JP2010/003965
§ 371 (c)(1),
(2), (4) Date: Jun. 6, 2012

(87) PCT Pub. No.: WO2011/077603
PCT Pub. Date: Jun. 30, 2011

(65) Prior Publication Data
US 2012/0242328 A1 Sep. 27, 2012

(30) Foreign Application Priority Data
Dec. 24, 2009 (JP) ................................. 2009-291799

(51) Int. Cl.
*G01N 27/74* (2006.01)
*G01R 33/12* (2006.01)

(52) U.S. Cl.
USPC ........................................................ 324/204

(58) Field of Classification Search
USPC ........................................................ 324/204
See application file for complete search history.

(56) References Cited

U.S. PATENT DOCUMENTS

| 4,841,244 A | 6/1989 | Chambers |
| 5,793,199 A | 8/1998 | Kasahara et al. |
| 8,037,740 B2 | 10/2011 | Fujii |
| 8,115,478 B2 | 2/2012 | Fujii et al. |
| 2012/0001619 A1 | 1/2012 | Ukai et al. |

FOREIGN PATENT DOCUMENTS

| JP | 62-93654 | 4/1987 |
| JP | 10-78409 | 3/1998 |
| JP | 10-132790 | 5/1998 |
| JP | 11-153541 | 6/1999 |

OTHER PUBLICATIONS

U.S. Appl. No. 13/256,119, filed Sep. 12, 2011, Ukai et al.
International Search Report issued Jul. 27, 2010 in PCT/JP2010/003965.

*Primary Examiner* — Reena Aurora
(74) *Attorney, Agent, or Firm* — Oblon, Spivak, McClelland, Maier & Neustadt, L.L.P.

(57) ABSTRACT

A magnetic particle producing part including magnetic and counterpart members in a path of a particle-includable liquid, at least one of the members being moved to press the other member in the liquid, the magnetic member being worn by particles in the liquid to produce magnetic particles; a magnetic particle measuring part positioned in the path same as in the producing part to measure the magnetic particle concentration in the liquid; and a control part converting the concentration of the magnetic particles detected by the measuring part into a concentration of particles in the liquid on the basis of a calibration line representing a correlation preliminarily measured between the concentrations of the magnetic particles and of the particles in the liquid to detect the concentration in the liquid.

9 Claims, 13 Drawing Sheets

RELATIONSHIP BETWEEN GRINDING TIME PERIOD AND
CONCENTRATION OF MAGNETIC POWDER (Fe)

CALIBRATION LINE REPRESENTING CORRELATION BETWEEN CONCENTRATIONS OF HARD PARTICLES AND OF MAGNETIC POWDER

US 8,816,674 B2

METHOD FOR DETECTING CONCENTRATION OF PARTICLES AND DEVICE THEREFOR

TECHNICAL FIELD

The invention relates to a method for detecting a concentration of particles in a liquid and a device therefor.

BACKGROUND ART

Generally, alumina, silica, carbon or other hard particles as residue in fluid catalytic cracking (FCC) for petroleum refinery are mixed in bunker C or other liquid as a main fuel for a marine diesel engine.

Excessive inflow of such particles into the engine, especially into a piston ring, a cylinder liner and the like of the engine, may cause adverse effects such as degraded sliding, seizing-up and mechanical wear. Thus, every time fuel is replenished, a ship management company samples and chemically analyzes the fuel to quantitatively grasp the particles in the fuel. When fuel with particles of not less than a stipulated concentration is replenished to a ship, the fact is notified of to the ship's crew to call their attention.

Conventionally, when particles in fuel are to be detected, sampled fuel is filtered through a filter or the like and a residue is microscopically observed or quantitatively analyzed to detect particles.

State-of-the-art technology with respect to a method for detecting a concentration of particles and a device therefor is shown, for example, in Patent Literature 1.

CITATION LIST

Patent Literature

[Patent Literature 1] JP 11-153541A

SUMMARY OF INVENTION

Technical Problems

However, any conventional method for detecting a concentration of particles and device therefor require a specific number of days until an analyzed result is reported to the ship's crew. Therefore, when the fuel requires to be used pending the analysis result, a problem arises that any adverse effects on the drive engine cannot be prevented in advance. A large amount of particles may be suddenly supplied to the engine when a particle-including contaminant is precipitated during storage to increase the concentration of the particles in the fuel or when malfunction of a filter, a centrifugal separation cleaner or the like occurs in a fuel treatment system from a fuel tank to an inlet of the engine. Thus, continuous and quantitative grasp of the particles in the fuel has been demanded.

There is also a problem that alumina, silica or other particles, which have no remarkable features in magnetism and in electric conductivity, are difficult to magnetically or electrically detect. There is further a problem that the particles, which are chemically stable, are difficult to detect utilizing a chemical reaction. There is still further a problem that the bunker C or the like liquid, which is opaque and highly viscous and includes various sludge or other particles in addition to the alumina and silica particles, cannot be sufficiently dealt with using optical determination as described in Patent Literature 1.

The invention was made in view of the above and has its object to provide a method for detecting a concentration of particles and a device therefor which grasp particles in a liquid quantitatively and continuously.

Solution to Problems

The invention is directed to a method for detecting a concentration of particles, providing a magnetic particle producing part positioned in a flow path of a liquid which may include particles and having magnetic and counterpart members arranged therein as well as a magnetic particle measuring part positioned in the flow path same as that for the magnetic particle producing part to measure a concentration of magnetic particles in the liquid, said method comprising the steps of, when a concentration of particles is to be measured, moving and pressing at least one of the members against the other member to produce magnetic particles in the liquid through wearing of the magnetic member, measuring a concentration of the magnetic particles produced in the liquid by the magnetic particle measuring part, converting the measured concentration of the magnetic particles into a concentration of particles in the liquid on the basis of a calibration line representing a correlation measured in advance between the concentrations of the magnetic particles and of the particles in the liquid, thereby detecting the concentration of the particles in the liquid.

In the method for detecting the concentration of the particles according to the invention, it is preferable that a concentration of magnetic particles originally included in the liquid is measured before the production of the magnetic particles by the magnetic particle producing part, said concentration of the magnetic particles originally included in the liquid being subtracted from the concentration of the magnetic particles produced in the liquid by the magnetic particle producing part, a subtracted result being converted into the concentration of the particles.

A device for detecting a concentration of particles according to the invention comprises a magnetic particle producing part having magnetic and counterpart members arranged in a flow path of a liquid which may include particles for moving and pressing at least one of said members against the other member to produce magnetic particles through wearing of the magnetic member, a magnetic particle measuring part positioned in the same flow path as that of the magnetic particle producing part for measuring the concentration of the magnetic particles in the liquid, and a control part for converting the concentration of the magnetic particles measured by the magnetic particle measuring part into a concentration of the particles in the liquid on the basis of a calibration line representing a correlation measured in advance between concentrations of the magnetic particles and of the particles in the liquid, thereby detecting the concentration of the particles in the liquid.

In the device for detecting the concentration of the particles according to the invention, it is preferable that a preceding magnetic particle measuring part is arranged upstream of the magnetic particle producing part to measure a concentration of the magnetic particles originally included in the liquid.

In the device for detecting the concentration of the particles according to the invention, it is preferable that the magnetic particle measuring part comprises a detector body connected to the flow path of the liquid, a movable partition adapted to communicate the flow path with an inside of the detector body such that the liquid in the flow path can be introduced into the detector body, an exciting coil positioned outside of the detector body, an output coil positioned outside of the detector body for generating an exciting voltage by an AC current of the exciting coil and a signal processing unit for measuring a variation in phase difference between the exciting and output coils.

In the device for detecting the concentration of the particles according to the invention, it is preferable that the detector body of the magnetic particle measuring part is arranged communicably with an inflow and outflow-side flow paths to and from the magnetic particle producing part, respectively, the movable partition of the magnetic particle measuring part comprising inflow- and outflow-side piston bodies arranged for the inflow- and outflow-side flow paths, respectively, an intermediate piston body arranged between the inflow- and outflow-side piston bodies and a piston rod having the inflow- and outflow-side and intermediate piston bodies arranged thereon, whereby movement of the piston rod in one direction brings about switching into a state where the inflow-side flow path is in communication with the inside of the detector body due to the inflow-side and intermediate piston bodies and the liquid flowing through the inflow-side flow path is introduced into the detector body; and movement of the piston rod in the other direction brings about switching into a state where the outflow-side flow path is in communication with the inside of the detector body due to the outflow-side and intermediate piston bodies and the liquid flowing through the outflow-side flow path is introduced into the detector body.

In the device for detecting the concentration of the particles according to the invention, it is preferable that the inflow-side flow path is provided with a temperature controlling unit for controlling a temperature on the inflow side and a flow adjusting unit for feeding the liquid at a constant flow rate.

Advantageous Effects of Invention

According to the method for detecting the concentration of particles and the device therefor of the invention, the following excellent effects can be obtained. The particles in the liquid can be quantitatively grasped by generating the particles through wearing of the magnetic material, measuring the concentration of the magnetic particles produced and converting the concentration of the magnetic particles into the concentration of the particles in the liquid by use of the calibration line to thereby detect the concentration of the particles in the liquid. The concentration of the particles in the liquid can be continuously grasped since the magnetic particle producing and measuring parts are provided in the same flow path. When the liquid is a fuel oil, the states can be prevented where untested fuel is used and where a large amount of particles are suddenly supplied to a driving engine, thereby suppressing any adverse effect on the drive engine. The fact that the concentration of the particles is indirectly detected using the magnetic particles produced by the wearing of the magnetic member eliminates the use of any operation and process for directly detecting the particles through physical or chemical treatment of the liquid itself so that favorably the particles in the liquid can be continuously and quantitatively grasped.

DESCRIPTION OF EMBODIMENT

An embodiment of the invention will be described with reference to FIGS. 1 to 12 which are illustrations of the method for detecting the concentration of particles and the device therefor. The embodiment will be described with respect to a case where a liquid flowing through a flow path is a fuel oil.

Figure 1:
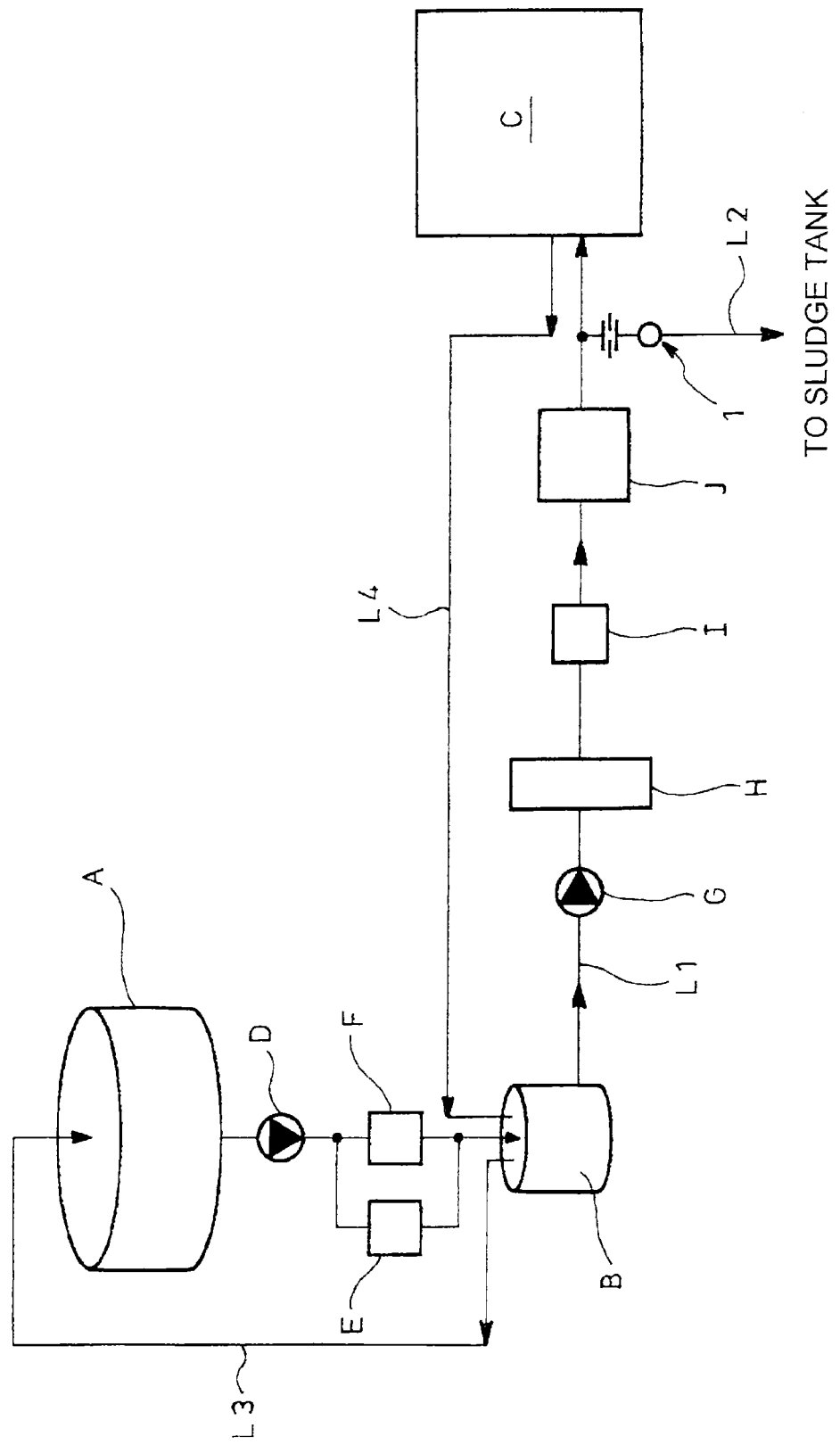
FIG. 1 is a conceptual view showing a position of a device for detecting a concentration of particles according to the invention.

As shown in FIG. 1, a device 1 for detecting a concentration of particles of the embodiment is arranged in a flow path L2 branched from a flow path L1 just before a prime mover C such that the concentration of particles (hard particles) can be measured without affecting the flow path L1 of the fuel oil from a fuel service tank A via a buffer column B into the prime mover C. The flow path L2 finally discharges the fuel measured by the detecting device 1 to a sludge tank (not shown). With the construction of FIG. 1, the flow path L has a fuel supply pump D, a bypass filter E, a fine filter F and the like in a portion from the fuel service tank A to the buffer column B, and has a circulation pump G, a heater H, a filter I and a viscosity adjuster J in a portion from the buffer column B to the prime mover C. Return flow paths L3 and L4 are arranged from the buffer column B to the tank A and from the prime mover C to the buffer column B, respectively.

Figure 2:
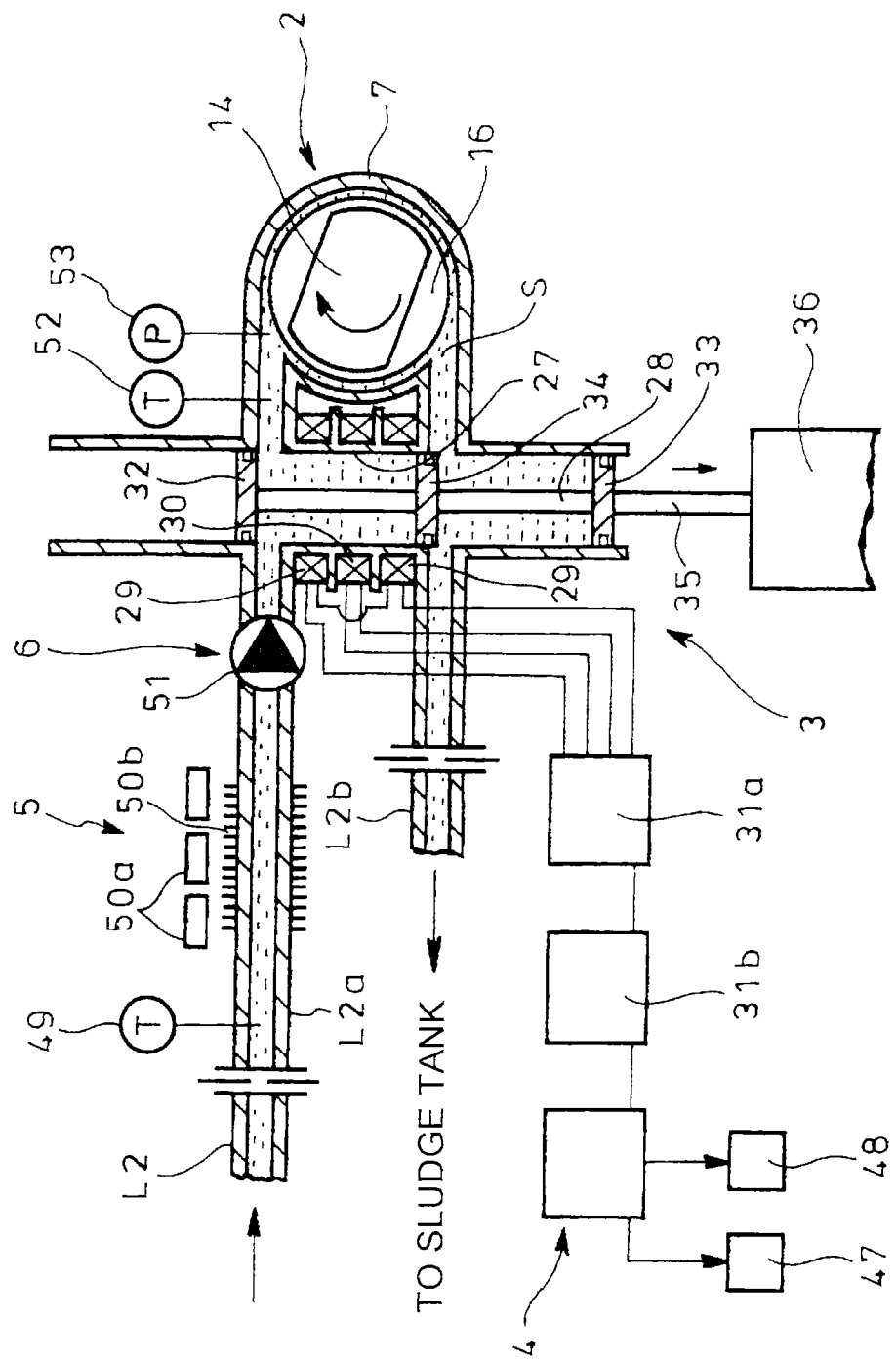
FIG. 2 is a general conceptual view showing the device for detecting the concentration of the particles according to the invention with a piston thereof being moved downward.
Figure 3:
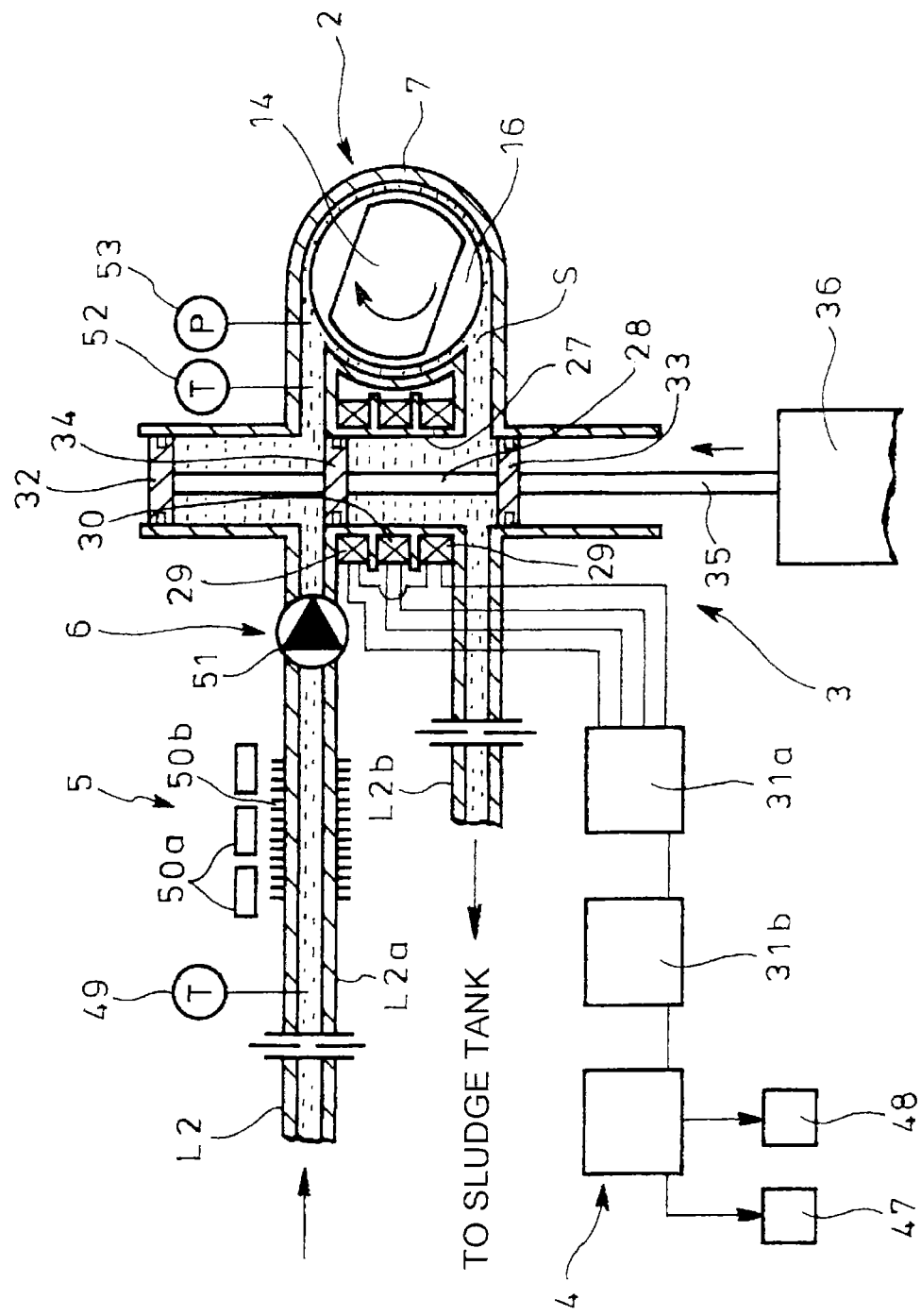
FIG. 3 is a general conceptual view showing the configuration of the device for detecting the concentration of the particles according to the invention with the piston thereof being moved upward.

The device 1 for detecting the concentration of the particles comprises, as shown in FIGS. 2 and 3, a magnetic particle producing part 2 positioned at a turnaround portion of the flow path L2 to produce magnetic particles in oil S, a magnetic particle measuring part 3 positioned in the flow path L2 just like the producing part 2 to measure a concentration of the magnetic particles in the oil S, a control part 4 to process information from the measuring part 3, a temperature controlling unit 5 positioned in an inflow-side flow path L2a to control a temperature on the inflow side and a flow adjusting unit 6 for a gear pump 51 positioned in the inflow-side flow path L2a to feed the oil S at a constant flow rate.

The magnetic particle producing part 2 comprises, as shown in FIGS. 2 to 4a, a casing 7 into/from which the oil S in the flow path L2 flows, a motor or other drive 8 positioned above the casing 7 and having a rotating shaft 8a, a disc-like rotating pedestal 10 positioned above within the casing 7 and connected through a connecting shaft 9 to the shaft 8a of the drive 8, a pedestal 12 positioned below within the casing 7 and biased upward from a bottom of the casing 7 by springs or other resilient members 11, a plate-like magnetic member 14 fixed to a bottom of the rotating pedestal 10 through a fixing pin or other fixing member 13 and a plate-like counterpart member 16 fixed to a top of the pedestal 12 through a fixing pin or other fixing member 15 and surface-contacting a bottom of the magnetic member 14. Seal rings 17 are arranged between the casing 7 and the connecting shaft 9 and between the casing 7 and the pedestal 12, respectively, to prevent the oil S from leaking outside. The magnetic member 14 is made of an iron-based or other material having magnetism. The counterpart member 16 is made of a carbon steel or other material which is harder and less wearable than the magnetic member 14. The material of the magnetic member 14 is not limited to iron and may be any, provided that magnetic particles with a required particle diameter can be produced due to the wearing. The material of the counterpart member 16 may be different from or the same as that of the magnetic member 14, provided that it can produce the magnetic particles from the magnetic member 14. The magnetic and counterpart members 14 and 16 may be arranged with their positions exchanged.

Figure 4A:
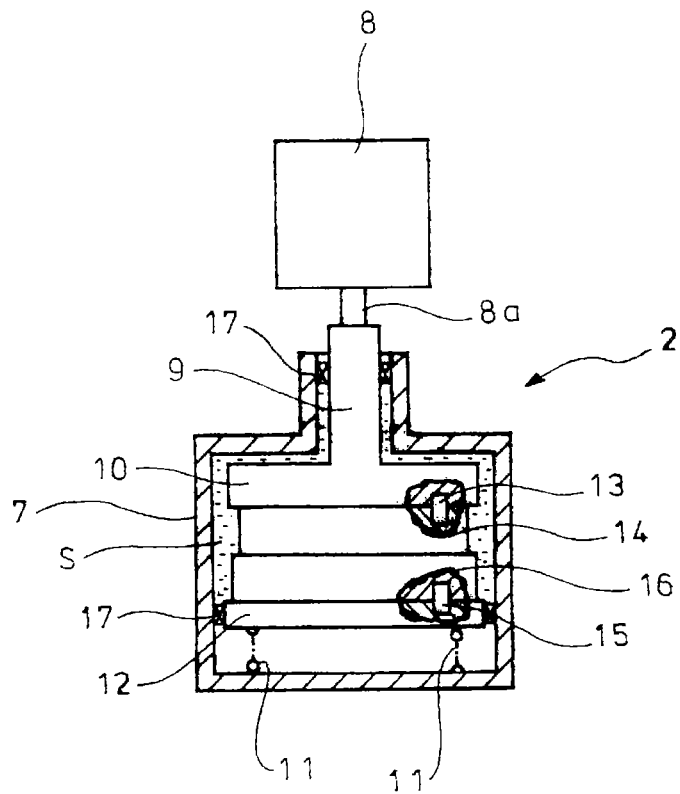
FIG. 4a is a conceptual view showing a magnetic particle producing part.
Figure 4B:
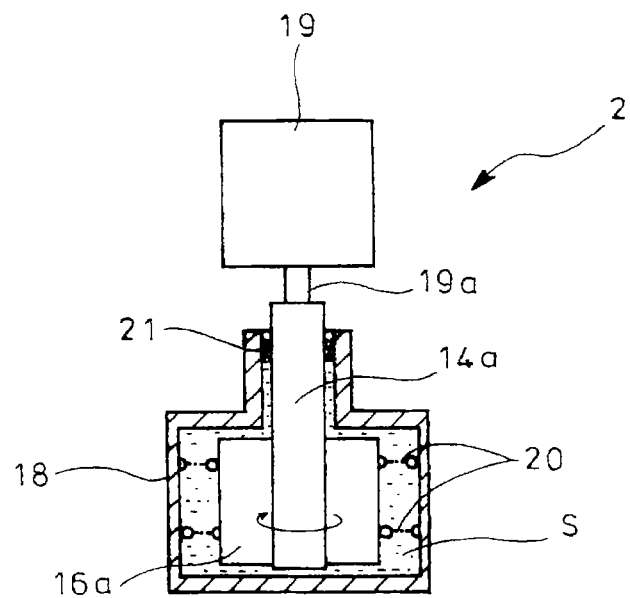
FIG. 4b is a conceptual view showing a modification of the magnetic particle producing part.

A modification of the magnetic particle producing part 2 is as shown in FIG. 4b and comprises a casing 18 into/from which the oil S in the flow path L2 flows, a motor or other drive 19 positioned above the casing 18 and having a shaft 19a, a rod-like magnetic member 14a connected to the shaft 19a of the drive 19 and rotatable in the casing 18 and a counterpart member 16a fitted over the magnetic member 14a and biased away from a side surface of the casing 18 by springs or other resilient members 20. A seal ring 21 is fitted between the casing 18 and the magnetic member 14a to prevent the oil S from leaking outside. The magnetic member 14a is made of an iron-based or other material having magnetism. The counterpart member 16a is made of carbon steel or other material which is harder and less wearable than the magnetic member 14a. The material of the magnetic member 14a is not limited to iron and may be any, provided that magnetic particles with a required particle diameter can be produced due to wearing. The material of the counterpart member 16a may be different from or the same as that of the magnetic member 14a, provided that it can produce the magnetic particles from the magnetic member 14a. The magnetic and counterpart members 14a and 16a may be arranged with their positions exchanged.

Figure 4C:
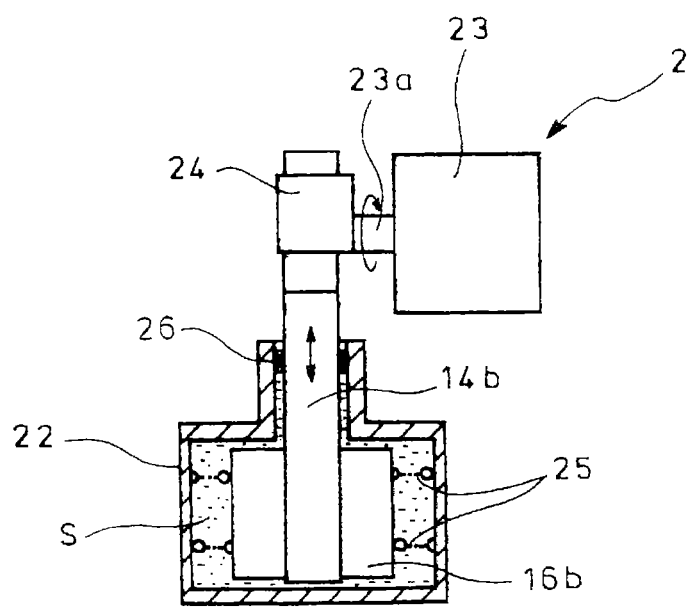
FIG. 4c is a conceptual view of a further modification of the magnetic particle producing part.

A further modification of the magnetic particle producing part 2 is as shown in FIG. 4c and comprises a casing 22 into/from which the oil S in the flow path L2 flows, a motor or other drive 23 positioned above the casing 22 and having a shaft 23a, a converter 24 which converts rotation of the shaft 23a into a reciprocating motion using an eccentric pin or the like, a rod-like magnetic member 14b connected to the converter 24 to move up and down in the casing 22 and a counterpart member 16b fitted over the magnetic member 14b and biased away from a side surface of the casing 22 through springs or other resilient members 25. A seal ring 26 is fitted between the casing 22 and the magnetic member 14b to prevent the oil S from leaking outside. The magnetic member 14b is made of an iron-based or other material having magnetism. The counterpart member 16b is made of carbon steel or other material which is harder and less wearable than the magnetic member 14b. The material of the magnetic member 14b is not limited to iron and may be any, provided that magnetic particles with a required particle diameter can be produced due to wearing. The material of the counterpart member 16b may be different from or the same as that of the magnetic member 14b, provided that it can produce the magnetic particles from the magnetic member 14b. The magnetic and counterpart members 14b and 16b may be arranged with their positions exchanged.

Figure 5:
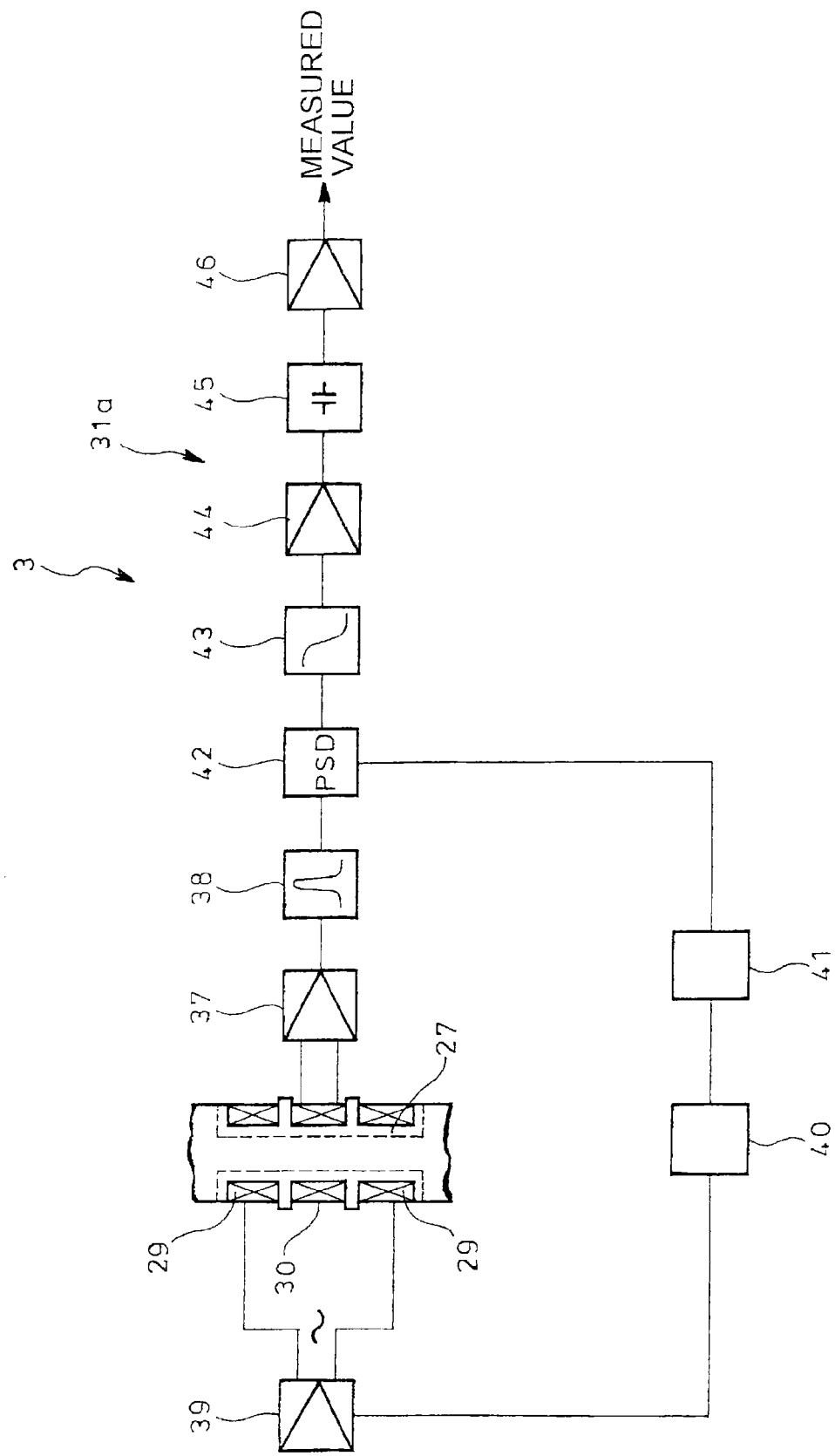
FIG. 5 is a block diagram showing a configuration of a signal processing unit in a magnetic particle measuring part.

The magnetic particle measuring part 3 comprises, as shown in FIGS. 2, 3 and 5, a detector body 27 connected to the flow path L2 for the oil S, a movable partition 28 adapted to communicate the flow path L2 with an inside of the detector body 27 such that the oil S in the flow path L2 can be introduced into the detector body 27, two exciting coils 29 positioned outside of the detector body 27, an output coil 30 positioned outside of the detector body 27 and adjacent to the exciting coils 29, a signal processing unit 31a connected to the coils 29 and 30 and a concentration measuring unit 31b for conversion of a signal of the signal processing unit.

The detector body 27 is arranged communicably with inflow- and outflow-side flow paths L2a and L2b to and from the magnetic particle producing part 2, respectively, for intercommunication therebetween. One and the other end of the detector body 27 extend outside of the flow paths L2a and L2b, respectively.

The movable partition 28 comprises an inflow-side piston body 32 which can move to provide a portion of an outside wall of the flow path L2a, an outflow-side piston body 33 which can move to provide a portion of an outside wall of the flow path L2b, an intermediate piston body 34 positioned between the inflow- and outflow-side piston bodies 32 and 33, a piston rod 35 having the piston bodies 32, 33 and 34 arranged thereon and a drive 36 such as a rotating body or a crank for reciprocating motion of the piston rod 35. Movement of the piston rod 35 in one direction (downward) as shown in FIG. 2 brings about switching into a state where the inflow-side flow path L2a is in communication with the inside of the detector body 27 due to the inflow-side and intermediate piston bodies 32 and 34, so that the oil S can flow through the flow path L2a and the inside of the detector body 27. On the other hand, movement of the piston rod 35 in the other direction (upward) as shown in FIG. 3 brings about switching into a state where the outflow-side flow path L2b is in communication with the inside of the detector body 27 due to the outflow-side and intermediate piston bodies 33 and 34, so that the oil S can flow through the flow path L2b and the inside of the detector body 27. Furthermore, the oil S introduced into the detector body 27 on the side of the inflow-side flow path L2a is pushed out from the inside of the detector body 27 into the inflow-side flow path L2a and outside in the one direction by the detector bodies 32 and 34 and is guided downstream by newly flowing oil S when the piston rod 35 is moved in the other direction (upward); the oil S introduced into the detector body 27 on the side of the outflow-side flow path L2b is pushed out from the inside of the detector body 27 into the outflow-side flow path L2b and outside in the other direction by the detector bodies 33 and 34 and is guided downstream by oil S newly flowing into the outflow-side flow path L2b when the piston rod 35 is moved in the one direction (downward). In the reciprocating movement of the piston rod 35, the intermediate piston body 34 is caused to move from an inner wall of the flow path L2a to an inner wall of the flow path L2b or vice versa so as to cause the oil S to flow between the two exciting coils 29 and the output coil 30.

The exciting coils 29 are two coils wound in directions opposite to each other, connected in series and arranged at a predetermined spacing from each other. The output coil 30 is arranged between and adjacent to the exciting coils 29. The output coil 30 is adapted to generate an output signal of an AC voltage (exciting voltage) when the AC voltage is applied to the exciting coils 29. The exciting and output coils 29 and 30 are adjusted to have substantially uniform mutual inductance by adjusting the wound number and distance of the coils. The exciting and output coils 29 and 30 have no limitation in their numbers; one exciting coil 29 and one output coil 30 may be used.

The signal processing unit 31a comprises, in order to acquire detection or corrective detection signal of the magnetic particles from the output signal of the output coil 30 as shown in FIG. 5, an amplifier circuit 37 connected to the coil 30 to amplify a feeble waveform signal, a band-pass filter 38 connected to the circuit 37 to remove noises in the waveform signal in a predetermined range, a sine wave oscillating circuit 39 connected to the exciting coils 29 to acquire a sine wave for excitation, a phase circuit 40 connected to the circuit 39 to shift the phase of the sine wave and an edge-trigger circuit 41 connected to the circuit 40 to convert the sine wave into a rectangular wave.

It is preferable that the phase circuit 40 shifts, upon setting or adjustment and with no magnetic particles being detected, the phase by 10°-170°, preferably by 45°-135°, and further preferably by about 90°. The phase circuit 40 may be alternatively positioned between the band-pass filter 38 and a signal processor 42 to shift not the phase of the reference signal, but the phases of the detection and corrective detection signals of the magnetic particles.

The signal processing unit 31a further comprises the signal processor 42 connected to the band-pass filter 38 and to the edge-trigger circuit 41, a low-pass filter 43 connected to the processor 42 to convert the output signal into a DC voltage signal, an amplifier 44 connected to the filter 43 to amplify the DC voltage signal, an AC signal transmission circuit 45 connected to the amplifier 44 for transmission of only an amount varied of the DC voltage signal due to the guided inflow/outflow of the oil S and an amplifier 46 connected to the circuit 45. The signal processor 42 is preferably a lock-in amplifier; however, it may be any, provided that it can measure variation in phase difference.

The concentration measuring unit 31b shown in FIGS. 2 and 3 is connected to the amplifier 46 in the signal processing unit 31a (see FIG. 5) for conversion into the concentration (concentration signal) of the magnetic particles on the basis of a measured value.

Figure 6:
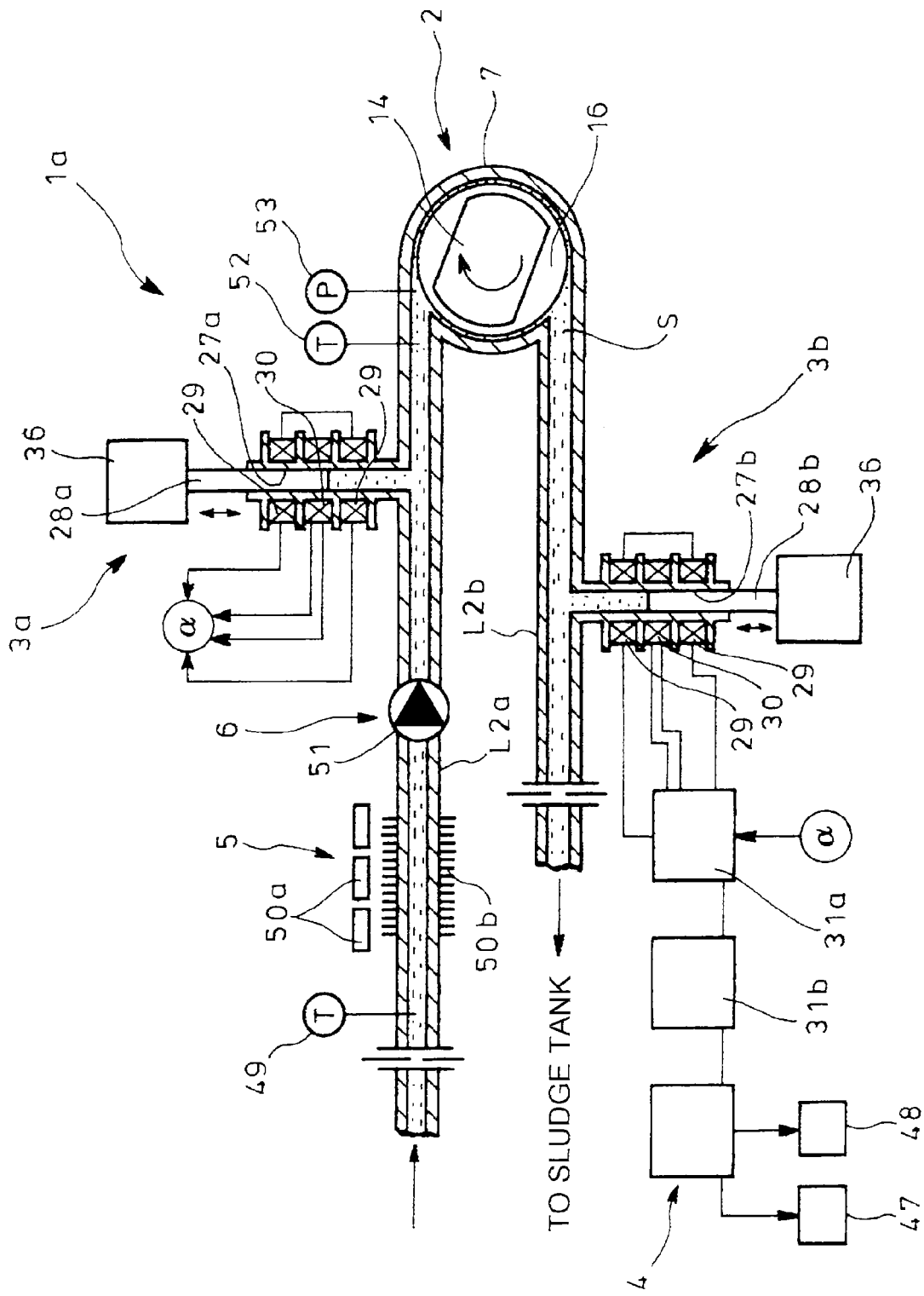
FIG. 6 is a general conceptual view showing a modification of the device for detecting the concentration of the particles according to the invention.

As shown in FIG. 6, alternatively, the magnetic particle measuring part 3 may be arranged as succeeding and preceding magnetic particle measuring parts 3b and 3a in the outflow- and inflow-side flow paths L2b and L2a, respectively. In this case, the succeeding magnetic particle measuring part 3b comprises a detector body 27b connected only to the inflow-side flow path L2 and a piston 28b which guides the oil S from the flow path L2 to the detector body 27b and vice versa, and is similar in the other configuration to that shown in FIG. 2. The preceding magnetic particle measuring part 3a comprises a detector body 27a connected only to the inflow-side flow path L2 and a piston 28a which guides the oil S from the flow path L2 to the detector body 27 and vice versa, and is adapted to send signals from the exciting and output coils 29 and 30 to the signal processor of the succeeding magnetic particle measuring unit 3b. A reference symbol α in the upper portion of FIG. 6 indicates connection to another reference symbol α in the lower portion thereof.

The control part 4 shown in FIGS. 2 and 3 is connected to the concentration measuring unit 31b of the magnetic particle measuring part 3 and is adapted to convert the concentration (concentration signal) of the magnetic particles measured by the measuring part 3 into the concentration of particles in the oil S by contrast with a calibration line (see FIG. 10) representing the correlation between the concentrations of the magnetic particles and of the particles in the oil S. The control part 4 includes a displaying unit 47 to display the concentration of the particles and a warning unit 48 to output a warning sound, warning indication or the like.

Figure 9:
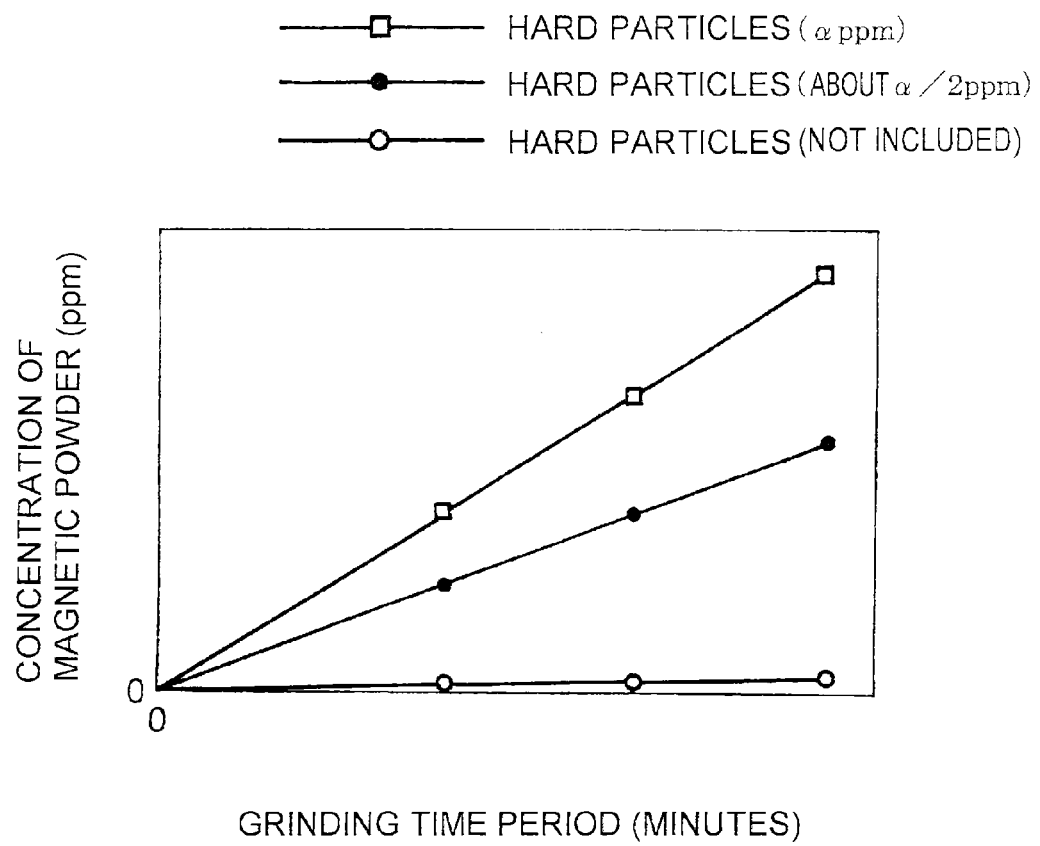
FIG. 9 is a graph showing a relationship between a drive time period (grinding time period) and a concentration of magnetic particles (magnetic powder Fe) in the magnetic particle producing part.
Figure 10:
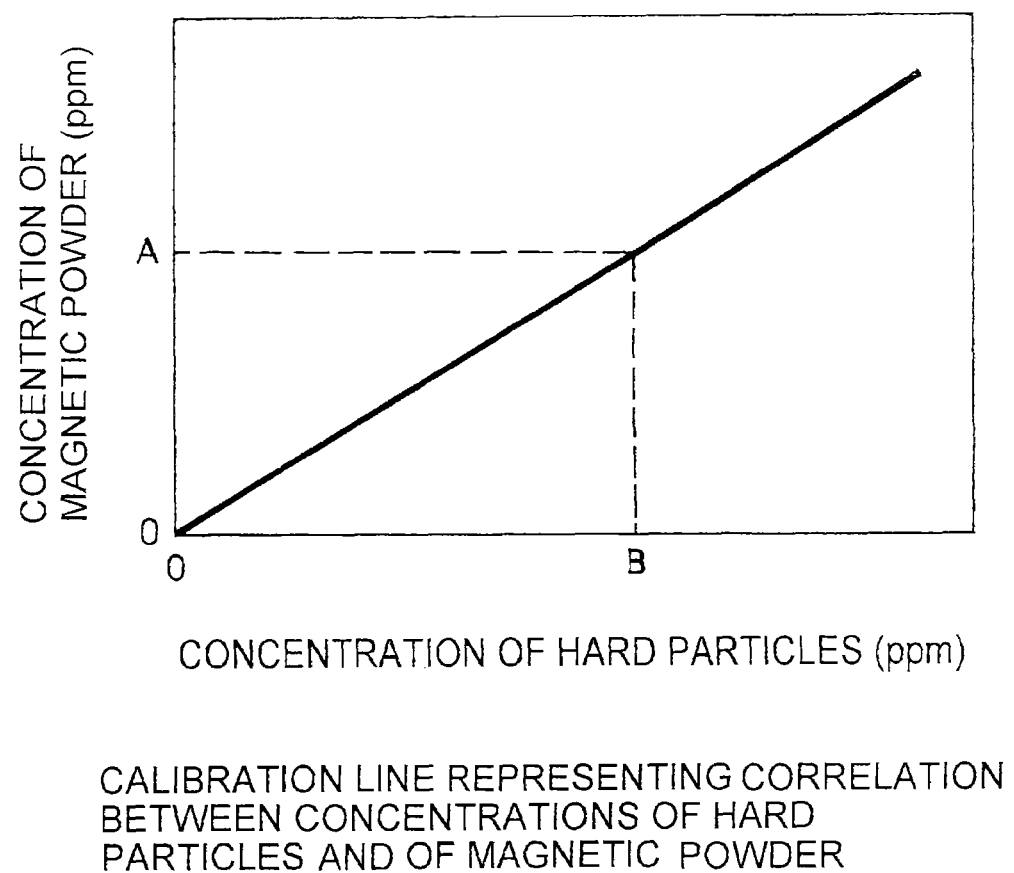
FIG. 10 shows a calibration line representing a relationship between concentrations of particles (hard particles) and of the magnetic particles (magnetic powder)

Testing of a relationship between the drive time period (grinding time period) of the magnetic particle producing part 2 and the concentration of the magnetic particles (magnetic powder Fe) revealed that the concentration of the magnetic particles in the oil S was linearly increased with elapse of the grinding time period (see FIG. 9). With the concentration of the particles originally included in the oil S being varied to α ppm, about α/2 ppm and no particle included (zero ppm) as shown in FIG. 9, it turned out that the concentrations of the particles and of the magnetic particles produced were similarly in a proportional relationship. Thus, the calibration line of the control part 4 is produced by comparing the concentrations of the particles (hard particles) and of the magnetic particles (magnetic powder) under the condition that the drive time period (grinding time period) of the magnetic particle producing part 2 is made constant.

The temperature controlling unit 5 comprises a thermometer 49 positioned upstream of the inflow-side flow path L2a and cooling fans and fins 50a and 50b positioned between the thermometer 49 and the magnetic particle measuring part 3 so as to cool down the inflow-side flow path L2a. The flow adjusting unit 6 comprises a gear pump 51 positioned between the temperature controlling unit 5 and the measuring part 3. A thermometer 52 and a pressure gauge 53 are arranged in the inflow-side flow path L2a between the magnetic particle measuring and producing parts 3 and 2.

An operation of the embodiment according to the invention will be described.

Figure 7:
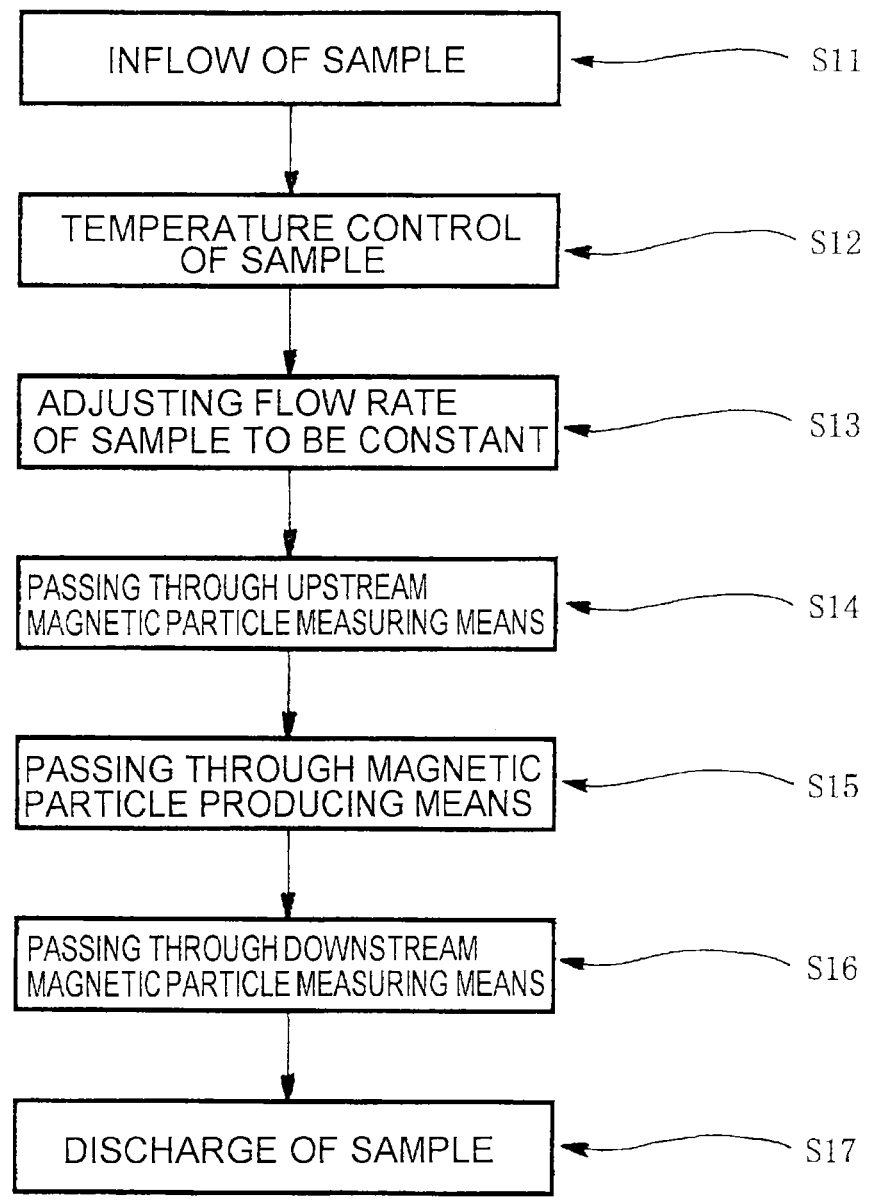
FIG. 7 is a flowchart of fluid flow in a method for detecting a concentration of particles according to the invention.

When the fuel or other oil (sample) S which may include particles is to be tested, the oil S is caused to flow into the particle concentration detecting device 1 in the flow path L2 branching just before the prime mover C (step S11 in FIG. 7). The fuel or other oil S to be tested is not limited to bunker C or other heavy oil and may be other type of oil such as gasoline, kerosene or light oil, provided that it may include particles. The use of the oil S is not limited to supply to the driving motor C of a ship or the like and may be supply to various kinds of driving engines and devices of, for example, a turbine plant. Water or a water solution may be used instead of the oil S; the liquid is not especially limited, provided that it may include particles. In addition, when water or a water solution is to be tested, the embodiment may be used for detection of particle-like impurities mixed in circulation water of a water circulation compressor or the like, may be used for a water quality inspection of operating water of a hydraulic machine and may be used for water quality management of treated water in a water treatment facility. In addition, particles are non-conductive and non-magnetic hard particles included in a liquid such as the oil S or water and capable of wearing the magnetic member 14 and are not limited to alumina, silica or carbon particles.

In the device 1 for detecting the concentration of the particles, firstly the temperature of the oil (sample) S is measured by the thermometer 49 in the temperature controlling unit 5. On the basis of the measured temperature of the oil S, the inflow-side cooling-down is conducted as needs demand by the cooling fan 50a or the like to control the temperature of the oil S (step S12). In the case of the fuel oil S flowing from the buffer column B to the driving motor C, the temperature of the oil S may be one hundred and several ten degrees; it is, therefore, preferable that the oil S is cooled to 40 to 60 degrees so as not to affect on the measurement by the magnetic particle measuring part 3 and the durability of the magnetic particle measuring and producing parts 3 and 2.

The flow adjusting unit 6 for the gear pump 51 adjusts a flow rate of the oil (specimen) S to be constant and decreases the pressure (step S13) to thereby stabilize the measurement and the processing by the magnetic particle measuring and producing parts 3 and 2, respectively.

Then, during passing of the oil (sample) S through the magnetic particle measuring part 3 in the inflow-side or upstream flow path L2 (step S14), the piston rod 35 is moved in one direction (downward in FIG. 2) for switching into a state where the inflow-side flow path L2a is communicated with the inside of the detector body 27 due to the inflow-side and intermediate piston bodies 32 and 34, so that the oil S flowing from the outflow-side flow path L2a into the magnetic particle producing part 2 is introduced into the detector body 27 for measurement of the concentration signal of the magnetic particles originally included in the oil S.

Then, during passing of the oil (sample) S through the magnetic particle producing part 2 (step S15), the drive 8 is driven to rotate and press the magnetic member 14 against the counterpart member 16 through the connecting shaft 9, the rotating pedestal 10 and the like, so that the magnetic member 14 is abrasively worn by particles entering between the magnetic and counterpart members 14 and 16 to produce the magnetic particles in the oil S. In the other configuration of the magnetic particle producing part 2 shown in FIG. 4b or 4c, similarly, the magnetic member 14a or 14b is abrasively worn to produce the magnetic particles in the oil S. The viscosity of the oil S is maintained constant so that, when the pressing pressure between the members 14 and 16 is kept properly, the magnetic particles (iron powder) are produced only by the particles (hard particles) not less than a specific size. The particles less than the specific size only pass through the gap between the members 14 and 16 and produce no magnetic particles. For the case of the magnetic member 14a or 14b and the counterpart member 16a or 16b, similarly, the magnetic particles (iron powder) are produced only by particles not less than a specific size and the particles less than the specific size produce no magnetic particles.

Then, during passing of the oil (sample) S through the magnetic particle measuring part 3 in the outflow-side or downstream flow path L2 (step S16), the piston rod 35 is moved in the other direction (upward in FIG. 3) for switching into a state where the flow path L2b is in communication with the inside of the detector body 27 due to the outflow-side and intermediate piston bodies 33 and 34, so that the oil S flowing from the magnetic particle producing part 2 to the outflow-side flow path L2b is introduced into the detector body 27 for measurement of the concentration signal of the magnetic particles on the outflow side. After detection of the concentration of the magnetic particles in the outflow-side flow path L2b, the oil S is returned to the flow path L2b through the movement of the movable partition 28 of the magnetic particle measuring part 3 and is discharged from the flow path L2b to the sludge tank (see FIG. 1) through an orifice (not shown) or the like (step S17).

Figure 8:
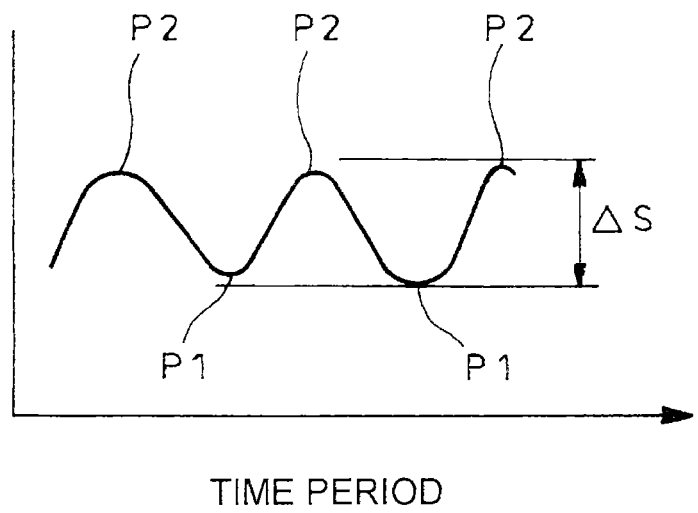
FIG. 8 is a graph showing a relationship between a time period and signals corresponding to concentrations of the magnetic particles when a movable partition of the magnetic particle measuring part is driven.

For measurement of the concentration of the magnetic particles, the piston rod 35 of the movable partition 28 is continuously reciprocated to alternately execute the measurements in the state where the oil S in the inflow-side flow path L2a is introduced into the detector body 27 and in the state where the oil S in the outflow-side flow path L2b is introduced into the detector body 27. The concentration (concentration signal) P1 of the magnetic particle originally included in the oil S is subtracted from the concentration (concentration signal) P2 of the outflow side magnetic particles as shown in FIG. 8 to calculate the concentration (concentration signal) ΔS of the magnetic particles produced by the magnetic particle producing part 2. In FIG. 8, P1 and P2 are positions at which the movable partition 28 of the magnetic particle measuring part 3 introduces the oil S from the inflow- and outflow-side flow paths L2a and L2b, respectively.

Figure 11:
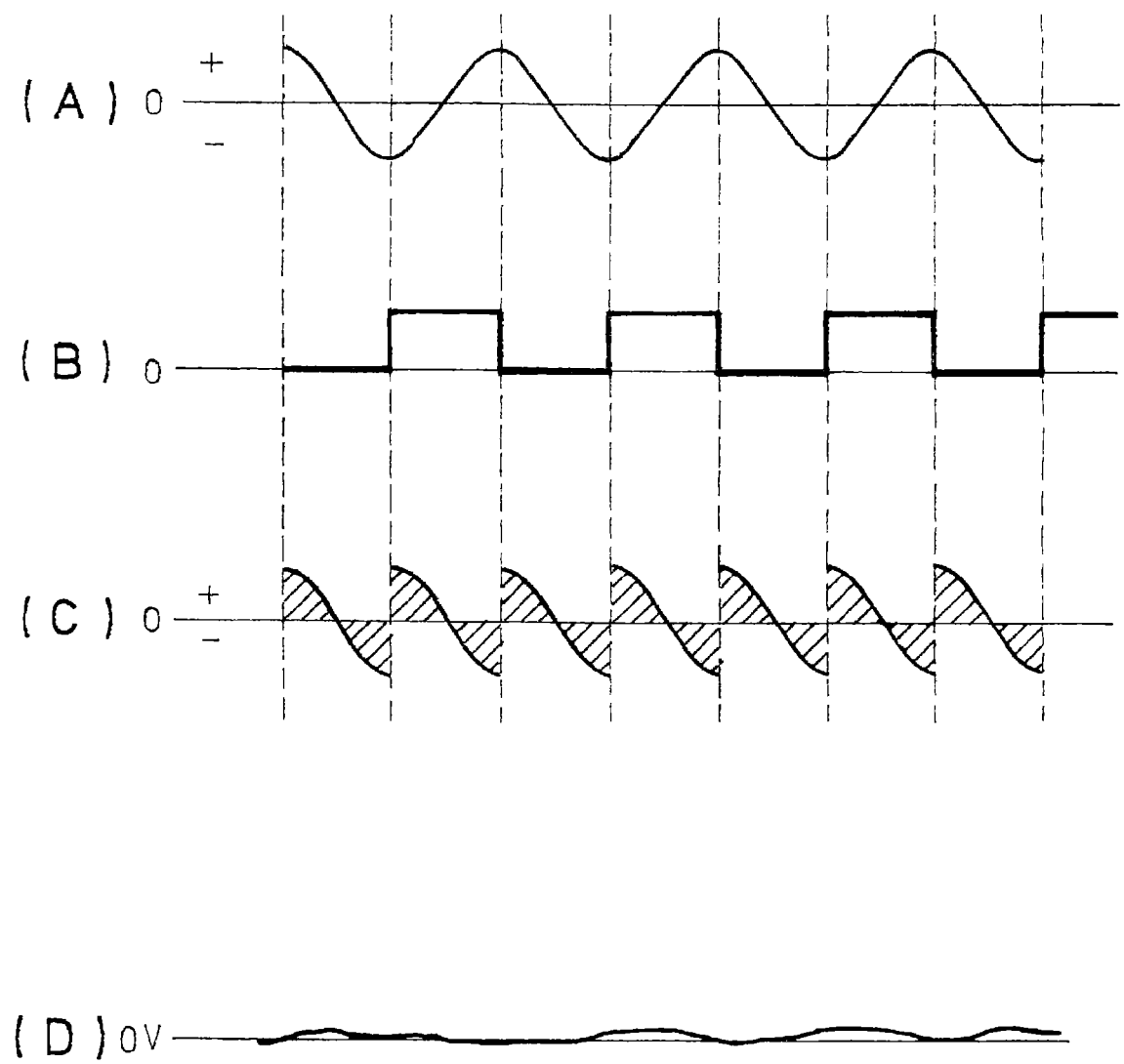
FIG. 11 is a conceptual view showing a process from output signals of the exciting and output coils to the output value for comparison.
Figure 12:
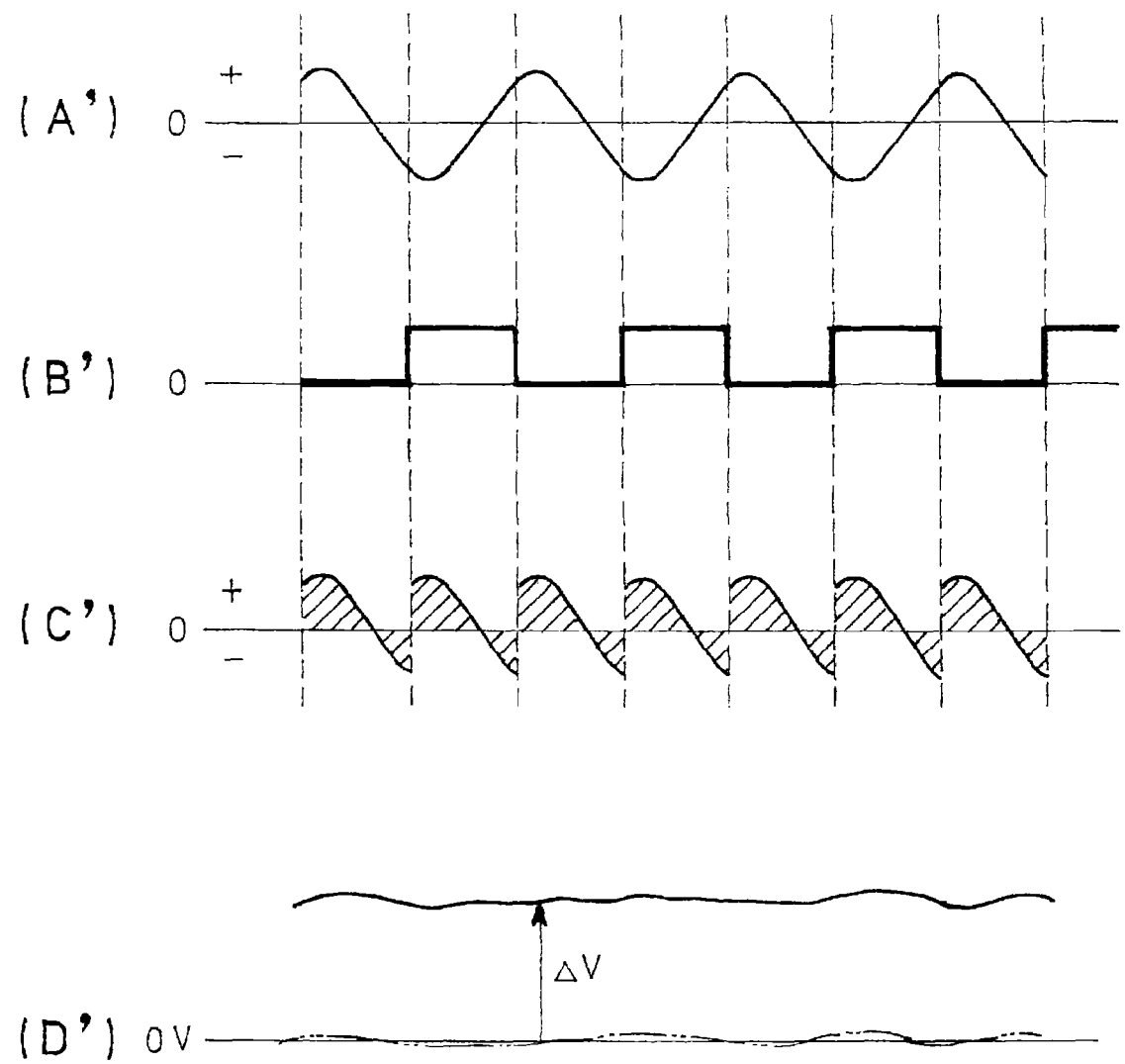
FIG. 12 is a conceptual view showing a process from the output signals of the exciting and output coils to the output value for the concentration of the magnetic particles.

The process of measuring the concentration of the magnetic particles by the signal processing unit 31a and the concentration measuring unit 31h will be described in detail (see FIGS. 11 and 12). When the oil S is introduced from the inflow-side flow path L2a into the detector body 27, the signal processing unit 31a acquires the corrective detection signal ((A) in FIG. 11) from the detector body 27 through the output coil 30, the amplifier circuit 37 and the band-pass filter 38 while the exciting coils 29, the sine wave oscillating circuit 39, the phase circuit 40 and the edge-trigger circuit 41 are used to prepare, through a phase shift by a predetermined angle, a rectangular-wave reference signal which is at a same frequency as that of the exciting voltage and which generates a specific phase difference relative to the exciting voltage ((B) in FIG. 11 with a phase shift of about) 90°. The signal processor 42 executes noise removal for the corrective detection signal together with the reference signal, and detects the phase difference between the corrective detection signal and the reference signal. The low-pass filter 43 converts the phase difference into a smooth DC voltage signal as the output value (the concentration of the magnetic particles originally included in the flow path L2) for the comparison ((D) in FIG. 11) which is inputted through the amplifier 44 into the AC signal transmission circuit 45. On the other hand, when the oil S is introduced from the outflow-side flow path L2b into the detector body 27, a detection signal of the magnetic particles is acquired ((A') in FIG. 12) from the oil S through the output coil 30, the amplifier circuit 37 and the band-pass filter 38 while the exciting coils 29, the sine wave oscillating circuit 39, the phase circuit 40 and the edge-trigger circuit 41 are used to prepare, through a phase shift by a predetermined angle, a rectangular-wave reference signal which is at a same frequency as that of the exciting voltage and which generates a specific phase difference relative to the exciting voltage ((B') in FIG. 12 with a phase shift of about 90°). The signal processor 42 executes noise removal for the detection signal together with the reference signal, and detects the phase difference between the detection signal of the magnetic particles and the reference signal. The low-pass filter 43 converts the phase difference into a smooth DC voltage signal as the output value for the concentration of the magnetic particles ((D') in FIG. 12) which is inputted through the amplifier 44 into the AC signal transmission circuit 45. To subtract the concentration of the magnetic particles originally included in the flow path L2, the AC signal transmission circuit 45 acquires a difference ΔV from the output value for the concentration of the magnetic particles and the output value for the comparison as shown in FIG. 12; the measured value is transmitted through the amplifier 46 to the concentration measuring unit 31b which then converts the measured value of the difference into a concentration (concentration signal) ΔS of the magnetic particles based on the correlation (function process) acquired in advance between the difference and the concentration. (C) of FIG. 11 shows the state where the detection signal of the magnetic particles is inverted by the reference signal and conceptually shows that (D) of FIG. 11 is acquired by processing the area thereof by integration. (C') of FIG. 12 shows the state where the detection signal of the magnetic particles is inverted by the reference signal and conceptually shows that (D') of FIG. 12 is acquired by processing the area thereof by integration.

After the concentration ΔS of the magnetic particles is calculated, the control part 4 converts the concentration of the magnetic particles into the concentration of the particles in the oil S based on the calibration line and displays the concentration of the particles on the displaying unit 47. When the concentration of the particles exceeds a predetermined threshold value, the warning unit 48 outputs a warning sound, indication or the like. Alternatively, the concentration of the particles may be converted directly from the stage of the difference ΔV of the AC signal transmission circuit 45 into the concentration of the particles through no processing by the concentration measuring unit 31b or may be processed according to any other procedure. The predetermined threshold value may be properly set based on, for example, a permissible amount of particles which may flow into the driving motor C.

Thus, when the fuel or other oil S is to be supplied to the driving motor C of a ship or the like, the concentration of the alumina, silica and other particles is monitored on site to preliminarily avoid any adverse effect on the driving engine caused by the particles.

In the case of the modification of the device 1 for detecting the concentration of the particles shown in FIG. 6, the preceding and succeeding magnetic particle measuring parts 3a and 3b in the inflow- and outflow-side flow paths L2a and L2b separately measure the concentration (concentration signal) of the magnetic particles. The concentration (concentration signal) of the magnetic particles originally included in the oil S is subtracted from the concentration (concentration signal) of the magnetic particles on the outflow side to thereby calculate the concentration (concentration signal) of the magnetic particles produced by the magnetic particle producing part 2. The calculated concentration of the magnetic particles is converted by the control part 4 into the concentration of the particles in the oil S on the basis of the calibration line.

The process of measuring the concentration of the magnetic particles by the magnetic particle measuring part 3b shown in FIG. 6 will be described. The signal processing unit 31a acquires the difference ΔV of the AC signal transmission circuit 45 by comparing the case where the oil S is discharged from the detector body 27 with the case where the oil S is introduced into the detector body 27, and the concentration measuring unit 31b acquires the concentration of the magnetic particles from the difference ΔV. In the case of the magnetic particle measuring part 3a, the concentration of the magnetic particles is acquired in the same manner as that in the magnetic particle measuring part 3b.

Thus, according to the embodiment of the method for detecting the concentration of the particles and the device therefor, the magnetic particles are produced by wearing the magnetic member 14 due to the presence of the particles in the oil S; the concentration of the magnetic particles produced in the oil S is measured; and the concentration of the magnetic particles is converted into the concentration of the particles in the oil S on the basis of the calibration line to thereby detect the concentration of the particles included in the oil S. Thus, a specific number of days are not required to detect the concentration of the particles unlike the conventional measuring methods, and the particles in the oil S can be quantitatively grasped. At the same time, the magnetic particle producing and measuring parts 2 and 3 are arranged in the same flow path L2, so that the concentration of the particles in the liquid can be continuously grasped.

The continuous and quantitative grasp of the particles in the oil S can prevent states where untested fuel is used and where a large amount of particles are suddenly supplied to a driving engine, so that any adverse effect on the driving engine can be suppressed. The concentration of the particles is indirectly detected using the magnetic particles such as iron powder produced by the wearing of the magnetic member 14, which eliminates the use of any operation and process for direct detection of the particles through physical or chemical processing of the oil S itself and favorably enables continuous and quantitative grasp of the particles in the oil S.

According to the embodiment, the concentration of the magnetic particles originally included in the oil S is measured before the production of the magnetic particles by the magnetic particle producing part 2 and is subtracted from the concentration of the magnetic particles produced in the liquid by the producing part 2; and the subtraction result is converted into the concentration of the particles. By such measurement of the concentration of only the magnetic particles produced in the oil by the magnetic particle producing part 2, the particles in the oil S can be favorably grasped.

The detector body 27 in the magnetic particle measuring part 3 is arranged for communication with the inflow- and outflow-side flow paths L2a and L2b to and out of the magnetic particle producing part 2, respectively. The movable partition 28 of the magnetic particle measuring part 3 comprises the inflow-side piston body 32 arranged for the inflow-side flow path L2a, the outflow-side piston body 33 arranged for the outflow-side flow path L2b, the intermediate piston body 34 arranged between the inflow- and outflow-side piston bodies 32 and 33 and the reciprocating piston rod 35 having the piston bodies 32, 33 and 34 arranged thereon. The movement of the piston rod 35 in the one direction brings about switching into the state where the inflow-side flow path L2a is in communication with the inside of the detector body 27 due to the inflow-side and intermediate piston bodies 32 and 34 and the oil S flowing through the flow path L2a is introduced into the detector body 27. The movement of the piston rod 35 in the other direction brings about switching into the state where the outflow-side flow path L2b is in communication with the inside of the detector body 27 due to the outflow-side and intermediate piston bodies 33 and 34 and the oil S flowing through the flow path L2b is introduced from the flow path L2b into the detector body 27. Due to the above configuration, the single magnetic particle measuring part 3 can easily measure the concentration of the magnetic particles originally included in the liquid and properly measure the concentration of the magnetic particles by the magnetic particle producing part 2 to thereby favorably grasp the particles in the oil S.

It is to be understood that a method for detecting a concentration of particles and a device therefor according to the invention are not limited to the above illustrated embodiment and that various changes and modifications may be made without departing from the scope of the invention.

REFERENCE SIGNS LIST 1 concentration detecting device
2 magnetic particle producing part 3 magnetic particle measuring part
3a magnetic particle measuring part
3b magnetic particle measuring part
4 control part
5 temperature controlling unit
6 flow adjusting unit
14 magnetic member
14a magnetic member
14b magnetic member
16 counterpart member
16a counterpart member
16b counterpart member
27 detector body
27a detector body
27b detector body
28 movable partition
28a movable partition
28b movable partition
29 exciting coil
30 output coil
31a signal processing unit
32 inflow-side piston body
33 outflow-side piston body
34 intermediate piston body
35 piston rod
S oil (liquid)

The invention claimed is:

1. A method for detecting a concentration of hard particles, providing a magnetic particle producing part positioned in a flow path of a liquid which may include non-conductive and non-magnetic hard particles and having magnetic and counterpart members arranged therein as well as a magnetic particle measuring part positioned in the flow path same as that for the magnetic particle producing part to measure a concentration of magnetic particles in the liquid, said method comprising the steps of, when a concentration of hard particles is to be measured,
   moving and pressing at least one of the members against the other member to produce magnetic particles in the liquid through wearing of the magnetic member, measuring a concentration of the magnetic particles produced in the liquid by the magnetic particle measuring part, converting the measured concentration of the magnetic particles into a concentration of hard particles in the liquid on the basis of a calibration line representing a correlation measured in advance between the concentrations of the magnetic particles and of the hard particles in the liquid, thereby detecting the concentration of the hard particles in the liquid.

2. The method for detecting the concentration of the hard particles as claimed in claim 1, wherein a concentration of magnetic particles originally included in the liquid is measured before the production of the magnetic particles by the magnetic particle producing part, said concentration of the magnetic particles originally included in the liquid being subtracted from the concentration of the magnetic particles produced in the liquid by the magnetic particle producing part, a subtracted result being converted into the concentration of the hard particles.

3. A device for detecting a concentration of hard particles comprising:
   a magnetic particle producing part having magnetic and counterpart members arranged in a flow path of a liquid which may include non-conductive and non-magnetic hard particles for moving and pressing at least one of said members against the other member to produce magnetic particles through wearing of the magnetic member,
   a magnetic particle measuring part positioned in the same flow path as that for the magnetic particle producing part for measuring a concentration of the magnetic particles in the liquid, and
   a control part for converting the concentration of the magnetic particles measured by the magnetic particle measuring part into a concentration of the hard particles in the liquid on the basis of a calibration line representing a correlation measured in advance between concentrations of the magnetic particles and of the hard particles in the liquid, thereby detecting the concentration of the hard particles in the liquid.

4. The device for detecting the concentration of the hard particles as claimed in claim 3, further comprising a preceding magnetic particle measuring part arranged upstream of the magnetic particle producing part to measure a concentration of the magnetic particles originally included in the liquid.

5. The device for detecting the concentration of the hard particles as claimed in claim 4, wherein the magnetic particle measuring part comprises a detector body connected to the flow path of the liquid, a movable partition adapted to communicate the flow path with an inside of the detector body such that the liquid in the flow path can be introduced into the detector body, an exciting coil positioned outside of the detector body, an output coil positioned outside of the detector body for generating an exciting voltage by an AC current of the exciting coil and a signal processing unit for measuring a variation in phase difference between the exciting and output coils.

6. The device for detecting the concentration of the hard particles as claimed in claim 5, wherein the detector body of the magnetic particle measuring part is arranged communicably with inflow- and outflow-side flow paths to and from the magnetic particle producing part, respectively,
   the movable partition of the magnetic particle measuring part comprising inflow- and outflow-side piston bodies arranged for the inflow- and outflow-side flow paths, respectively, an intermediate piston body arranged between the inflow- and outflow-side piston bodies and a piston rod having the inflow- and outflow-side and intermediate piston bodies arranged thereon,
   whereby movement of the piston rod in one direction brings about switching into a state where the inflow-side flow path is in communication with the inside of the detector body due to the inflow-side and intermediate piston bodies and the liquid flowing through the inflow-side flow path is introduced into the detector body; and movement of the piston rod in the other direction brings about switching into a state where the outflow-side flow path is in communication with the inside of the detector body due to the outflow-side and intermediate piston bodies and the liquid flowing through the outflow-side flow path is introduced into the detector body.

7. The device for detecting the concentration of the hard particles as claimed in claim 3, wherein the magnetic particle measuring part comprises a detector body connected to the flow path of the liquid, a movable partition adapted to communicate the flow path with an inside of the detector body such that the liquid in the flow path can be introduced into the detector body, an exciting coil positioned outside of the detector body, an output coil positioned outside of the detector body for generating an exciting voltage by an AC current of the exciting coil and a signal processing unit for measuring a variation in phase difference between the exciting and output coils.

8. The device for detecting the concentration of the hard particles as claimed in claim 7, wherein the detector body of the magnetic particle measuring part is arranged communicably with inflow- and outflow-side flow paths to and from the magnetic particle producing part, respectively, the movable partition of the magnetic particle measuring part comprising inflow- and outflow-side piston bodies arranged for the inflow- and outflow-side flow paths, respectively, an intermediate piston body arranged between the inflow- and outflow-side piston bodies and a piston rod having the inflow- and outflow-side and intermediate piston bodies arranged thereon, whereby movement of the piston rod in one direction brings about switching into a state where the inflow-side flow path is in communication with the inside of the detector body due to the inflow-side and intermediate piston bodies and the liquid flowing through the inflow-side flow path is introduced into the detector body; and movement of the piston rod in the other direction brings about switching into a state where the outflow-side flow path is in communication with the inside of the detector body due to the outflow-side and intermediate piston bodies and the liquid flowing through the outflow-side flow path is introduced into the detector body.

9. The device for detecting the concentration of the hard particles as claimed in claim 3, wherein the inflow-side flow path is provided with a temperature controlling unit for controlling a temperature on the inflow side and a flow adjusting unit for feeding the liquid at a constant flow rate.

\* \* \* \* \*